United States Patent
Mothilal et al.

(10) Patent No.: US 9,351,648 B2
(45) Date of Patent: May 31, 2016

(54) IMPLANTABLE MEDICAL DEVICE ELECTRODE ASSEMBLY

(75) Inventors: Kamal D. Mothilal, Minneapolis, MN (US); George Patras, Greenfield, MN (US)

(73) Assignee: Medtronic, Inc., Minneapolis, MN (US)

(*) Notice: Subject to any disclaimer, the term of this patent is extended or adjusted under 35 U.S.C. 154(b) by 951 days.

(21) Appl. No.: 13/594,587

(22) Filed: Aug. 24, 2012

(65) Prior Publication Data

US 2014/0058240 A1    Feb. 27, 2014

(51) Int. Cl.
| | |
|---|---|
| A61B 5/00 | (2006.01) |
| A61B 5/0215 | (2006.01) |
| A61N 1/372 | (2006.01) |
| A61B 5/0205 | (2006.01) |
| A61B 5/0452 | (2006.01) |

(52) U.S. Cl.
CPC ............. *A61B 5/0215* (2013.01); *A61B 5/6861* (2013.01); *A61N 1/37205* (2013.01); *A61B 5/02055* (2013.01); *A61B 5/0452* (2013.01); *A61B 2562/162* (2013.01); *Y10T 29/49018* (2015.01)

(58) Field of Classification Search
CPC ..... A61N 1/372; A61N 1/375; A61N 1/3752; A61N 1/3758; A61N 1/0472; A61N 1/37205; A61B 5/0215; A61B 5/6861; Y10T 29/49018
USPC .................. 607/116; 600/300, 373
See application file for complete search history.

(56) References Cited

U.S. PATENT DOCUMENTS

| | | |
|---|---|---|
| 4,035,909 A | 7/1977 | Dey |
| 4,103,690 A | 8/1978 | Harris |
| 4,112,952 A | 9/1978 | Thomas et al. |
| 4,376,811 A | 3/1983 | Goebel |
| 4,731,305 A | 3/1988 | Goebel et al. |
| 4,760,849 A | 8/1988 | Kropf |

(Continued)

FOREIGN PATENT DOCUMENTS

| | | |
|---|---|---|
| EP | 0362611 A1 | 4/1990 |
| EP | 0897690 A1 | 2/1999 |

(Continued)

OTHER PUBLICATIONS

Medtronic, Inc., "Cardiac Resynchronization Therapy for Heart Failure Management—Implant and Follow-up—Brief Overview" 4 pages. (2002).

(Continued)

*Primary Examiner* — Christopher D Koharski
*Assistant Examiner* — Michael Carey

(57) ABSTRACT

An implantable medical device (IMD) includes an electrode that forms a first snap-fit attachment area and an insulator that forms a through-hole, a second snap-fit attachment area and a third snap-fit attachment area. The second snap-fit attachment area mates with the first snap-fit attachment area of the electrode. The IMD further includes a body including an elongated conductive housing and a feedthrough wire extending therefrom. The body forms a fourth snap-fit attachment area on one end that mates with the third snap-fit attachment area of the insulator such that the feedthrough wire extends through the through-hole of the insulator. The housing encloses at least one of a battery, a sensor, and an electronic circuit. The insulator functions to electrically isolate the electrode from the housing of the body.

19 Claims, 7 Drawing Sheets

(56) References Cited

U.S. PATENT DOCUMENTS

| | | |
|---|---|---|
| 4,913,147 A | 4/1990 | Fahlstrom et al. |
| 4,987,897 A | 1/1991 | Funke |
| 5,002,067 A | 3/1991 | Berthelsen et al. |
| 5,024,239 A | 6/1991 | Rosenstein |
| 5,147,330 A | 9/1992 | Kogel |
| 5,218,965 A | 6/1993 | Ring |
| 5,249,574 A | 10/1993 | Bush et al. |
| 5,255,678 A | 10/1993 | Deslauriers et al. |
| 5,255,679 A | 10/1993 | Imran |
| 5,265,608 A | 11/1993 | Lee et al. |
| 5,282,845 A | 2/1994 | Bush et al. |
| 5,284,138 A | 2/1994 | Kujawski |
| 5,306,581 A | 4/1994 | Taylor et al. |
| 5,314,451 A | 5/1994 | Mulier |
| 5,314,462 A | 5/1994 | Heil, Jr. et al. |
| 5,358,514 A | 10/1994 | Schulman et al. |
| 5,383,922 A | 1/1995 | Zipes et al. |
| 5,387,233 A | 2/1995 | Alferness et al. |
| 5,411,546 A | 5/1995 | Bowald et al. |
| 5,411,551 A | 5/1995 | Winston et al. |
| 5,415,630 A | 5/1995 | Gory et al. |
| 5,476,796 A | 12/1995 | Takahashi et al. |
| 5,480,416 A | 1/1996 | Garcia et al. |
| 5,492,119 A | 2/1996 | Abrams |
| 5,540,734 A | 7/1996 | Zabara |
| 5,545,219 A | 8/1996 | Kuzma |
| 5,576,019 A | 11/1996 | Paulos |
| 5,766,234 A | 6/1998 | Chen et al. |
| 5,772,668 A | 6/1998 | Summers et al. |
| 5,776,632 A | 7/1998 | Honegger |
| 5,800,520 A | 9/1998 | Fogarty et al. |
| 5,814,089 A | 9/1998 | Stokes et al. |
| 5,814,091 A | 9/1998 | Dahlberg et al. |
| 5,840,076 A | 11/1998 | Swanson et al. |
| 5,860,974 A | 1/1999 | Abele |
| 5,897,584 A | 4/1999 | Herman |
| 5,925,069 A | 7/1999 | Graves et al. |
| 5,927,277 A | 7/1999 | Baudino et al. |
| 5,967,986 A | 10/1999 | Cimochowski et al. |
| 5,988,171 A | 11/1999 | Sohn et al. |
| 6,015,387 A | 1/2000 | Schwartz et al. |
| 6,024,764 A | 2/2000 | Schroeppel |
| 6,053,873 A | 4/2000 | Govari et al. |
| 6,074,401 A | 6/2000 | Gardiner et al. |
| 6,113,593 A | 9/2000 | Tu et al. |
| 6,136,005 A | 10/2000 | Goode et al. |
| 6,149,658 A | 11/2000 | Gardiner et al. |
| 6,159,156 A | 12/2000 | Van Bockel |
| 6,183,305 B1 | 2/2001 | Doan et al. |
| 6,183,478 B1 | 2/2001 | Konieczynski |
| 6,214,036 B1 | 4/2001 | Letendre et al. |
| 6,221,024 B1 | 4/2001 | Miesel |
| 6,238,813 B1 | 5/2001 | Maile et al. |
| 6,249,709 B1 | 6/2001 | Conger et al. |
| 6,266,568 B1 | 7/2001 | Mann et al. |
| 6,277,078 B1 | 8/2001 | Porat et al. |
| 6,308,105 B1 | 10/2001 | Duysens et al. |
| 6,309,350 B1 | 10/2001 | Van Tassel et al. |
| 6,331,163 B1 | 12/2001 | Kaplan |
| 6,350,278 B1 | 2/2002 | Lenker et al. |
| 6,352,561 B1 | 3/2002 | Leopold et al. |
| 6,371,928 B1 | 4/2002 | Mcfann et al. |
| 6,416,474 B1 | 7/2002 | Penner et al. |
| 6,434,431 B1 | 8/2002 | Camps et al. |
| 6,442,413 B1 | 8/2002 | Silver |
| 6,468,301 B1 | 10/2002 | Amplatz et al. |
| 6,477,423 B1 | 11/2002 | Jenkins |
| 6,498,951 B1 | 12/2002 | Larson et al. |
| 6,505,075 B1 | 1/2003 | Weiner |
| 6,510,332 B1 | 1/2003 | Greenstein |
| 6,512,940 B1 | 1/2003 | Brabec et al. |
| 6,514,265 B2 | 2/2003 | Ho et al. |
| 6,529,777 B1 | 3/2003 | Holmström et al. |
| 6,551,332 B1 | 4/2003 | Nguyen et al. |
| 6,585,634 B1 | 7/2003 | Henckel et al. |
| 6,589,238 B2 | 7/2003 | Edwards et al. |
| 6,600,955 B1 | 7/2003 | Zierhofer |
| 6,607,541 B1 | 8/2003 | Gardiner et al. |
| 6,607,843 B2 | 8/2003 | Ruth, II et al. |
| 6,613,059 B2 | 9/2003 | Schaller et al. |
| 6,622,046 B2 | 9/2003 | Fraley et al. |
| 6,626,916 B1 | 9/2003 | Yeung et al. |
| 6,641,593 B1 | 11/2003 | Schaller et al. |
| 6,695,859 B1 | 2/2004 | Golden et al. |
| 6,783,499 B2 | 8/2004 | Schwartz |
| 6,821,291 B2 | 11/2004 | Bolea et al. |
| 6,855,115 B2 | 2/2005 | Fonseca et al. |
| 6,876,885 B2 | 4/2005 | Swoyer et al. |
| 6,889,093 B1 | 5/2005 | Flammang |
| 6,895,283 B2 | 5/2005 | Erickson et al. |
| 6,908,464 B2 | 6/2005 | Jenkins et al. |
| 6,909,920 B2 | 6/2005 | Lokhoff et al. |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,670 B2 | 8/2005 | Rich et al. |
| 6,926,730 B1 | 8/2005 | Nguyen et al. |
| 6,932,837 B2 | 8/2005 | Amplatz et al. |
| 6,960,221 B2 | 11/2005 | Ho et al. |
| 6,986,784 B1 | 1/2006 | Weiser et al. |
| 7,011,671 B2 | 3/2006 | Welch |
| 7,018,401 B1 | 3/2006 | Hyodoh et al. |
| 7,047,076 B1 | 5/2006 | Li et al. |
| 7,047,084 B2 | 5/2006 | Erickson et al. |
| 7,054,692 B1 | 5/2006 | Whitehurst et al. |
| 7,070,881 B2 | 7/2006 | Kishiyama et al. |
| 7,072,703 B2 | 7/2006 | Zhang et al. |
| 7,099,718 B1 | 8/2006 | Thacker et al. |
| 7,103,408 B2 | 9/2006 | Haller et al. |
| 7,128,765 B2 | 10/2006 | Paulot et al. |
| 7,166,127 B2 | 1/2007 | Spence et al. |
| 7,177,702 B2 | 2/2007 | Wallace et al. |
| 7,181,261 B2 | 2/2007 | Silver et al. |
| 7,181,288 B1 | 2/2007 | Rezai et al. |
| 7,182,725 B2 | 2/2007 | Bonan et al. |
| 7,211,107 B2 | 5/2007 | Bruckheimer et al. |
| 7,214,230 B2 | 5/2007 | Brock et al. |
| 7,240,516 B2 | 7/2007 | Pryor |
| 7,288,096 B2 | 10/2007 | Chin |
| 7,291,186 B2 | 11/2007 | Zhang |
| 7,309,354 B2 | 12/2007 | Mathis et al. |
| 7,410,512 B2 | 8/2008 | Tsukamoto et al. |
| 7,431,726 B2 | 10/2008 | Spence et al. |
| 7,452,334 B2 | 11/2008 | Gianchandani et al. |
| 7,463,934 B2 | 12/2008 | Tronnes et al. |
| 7,473,272 B2 | 1/2009 | Pryor |
| 7,481,771 B2 | 1/2009 | Fonseca et al. |
| 7,512,448 B2 | 3/2009 | Malick et al. |
| 7,546,165 B2 | 6/2009 | Zarembo et al. |
| 7,572,228 B2 | 8/2009 | Wolinsky et al. |
| 7,591,185 B1 | 9/2009 | Mothilal et al. |
| 7,647,110 B2 | 1/2010 | Hörnfeldt et al. |
| 7,655,039 B2 | 2/2010 | Leanna et al. |
| 7,682,313 B2 | 3/2010 | Bodecker et al. |
| 7,726,663 B2 | 6/2010 | Mack et al. |
| 7,727,270 B2 | 6/2010 | Rucker |
| 7,747,302 B2 | 6/2010 | Milledge et al. |
| 7,765,014 B2 | 7/2010 | Eversull et al. |
| 7,769,420 B2 | 8/2010 | Silver et al. |
| 7,771,463 B2 | 8/2010 | Ton et al. |
| 7,797,053 B2 | 9/2010 | Atkinson et al. |
| 7,799,067 B2 | 9/2010 | Pryor |
| 7,801,626 B2 | 9/2010 | Moser |
| 7,801,627 B2 | 9/2010 | Haldeman |
| 7,876,282 B2 | 1/2011 | Keilman et al. |
| 7,899,553 B2 | 3/2011 | Barker |
| 8,055,346 B2 | 11/2011 | Youker |
| 2001/0002300 A1 | 5/2001 | Tinker et al. |
| 2001/0047181 A1 | 11/2001 | Ho et al. |
| 2002/0010490 A1 | 1/2002 | Schaller et al. |
| 2002/0103521 A1 | 8/2002 | Swoyer et al. |
| 2002/0111659 A1 | 8/2002 | Davis et al. |
| 2002/0147485 A1 | 10/2002 | Mamo et al. |
| 2002/0147487 A1 | 10/2002 | Sundquist et al. |

(56) References Cited

U.S. PATENT DOCUMENTS

| | | |
|---|---|---|
| 2002/0156513 A1 | 10/2002 | Borkan |
| 2002/0161423 A1 | 10/2002 | Lokhoff et al. |
| 2002/0188207 A1 | 12/2002 | Richter |
| 2003/0023295 A1 | 1/2003 | Osypka |
| 2003/0029558 A1 | 2/2003 | Hochrainer et al. |
| 2003/0032936 A1 | 2/2003 | Lederman |
| 2003/0036790 A1 | 2/2003 | Corbett, III et al. |
| 2003/0069623 A1 | 4/2003 | Stypulkowski |
| 2003/0078603 A1 | 4/2003 | Schaller et al. |
| 2003/0088301 A1 | 5/2003 | King |
| 2003/0093118 A1 | 5/2003 | Ho et al. |
| 2003/0093130 A1 | 5/2003 | Stypulkowski |
| 2003/0120328 A1 | 6/2003 | Jenkins et al. |
| 2003/0125790 A1 | 7/2003 | Fastovsky et al. |
| 2003/0153966 A1 | 8/2003 | Taubert et al. |
| 2003/0199974 A1 | 10/2003 | Lee et al. |
| 2004/0044393 A1 | 3/2004 | Yarden et al. |
| 2004/0059393 A1 | 3/2004 | Policker et al. |
| 2004/0093053 A1 | 5/2004 | Gerber et al. |
| 2004/0101746 A1 | 5/2004 | Ota et al. |
| 2004/0102797 A1 | 5/2004 | Golden et al. |
| 2004/0111099 A1 | 6/2004 | Nguyen et al. |
| 2004/0111139 A1 | 6/2004 | McCreery |
| 2004/0116878 A1 | 6/2004 | Byrd et al. |
| 2004/0116992 A1 | 6/2004 | Wardle et al. |
| 2004/0176782 A1 | 9/2004 | Hanse et al. |
| 2004/0185337 A1 | 9/2004 | Ishizaki |
| 2004/0193229 A1 | 9/2004 | Starkebaum et al. |
| 2004/0230279 A1 | 11/2004 | Cates et al. |
| 2004/0243206 A1 | 12/2004 | Tadlock |
| 2005/0021054 A1 | 1/2005 | Ainsworth et al. |
| 2005/0033394 A1 | 2/2005 | Seifert et al. |
| 2005/0060014 A1 | 3/2005 | Swoyer et al. |
| 2005/0065601 A1 | 3/2005 | Lee et al. |
| 2005/0070924 A1 | 3/2005 | Schaller et al. |
| 2005/0090884 A1 | 4/2005 | Honeck |
| 2005/0096718 A1 | 5/2005 | Gerber et al. |
| 2005/0102006 A1 | 5/2005 | Whitehurst et al. |
| 2005/0107861 A1 | 5/2005 | Harris et al. |
| 2005/0149141 A1 | 7/2005 | Starkebaum |
| 2005/0149142 A1 | 7/2005 | Starkebaum |
| 2005/0154321 A1 | 7/2005 | Wolinsky et al. |
| 2005/0187482 A1 | 8/2005 | O'Brien et al. |
| 2005/0209653 A1 | 9/2005 | Herbert et al. |
| 2005/0222632 A1 | 10/2005 | Obino |
| 2005/0245840 A1 | 11/2005 | Christopherson et al. |
| 2005/0245986 A1 | 11/2005 | Starkebaum |
| 2005/0246004 A1 | 11/2005 | Cameron et al. |
| 2005/0277839 A1 | 12/2005 | Aldermun et al. |
| 2006/0047205 A1 | 3/2006 | Ludomirsky et al. |
| 2006/0057458 A1 | 3/2006 | O'Dea et al. |
| 2006/0069422 A9 | 3/2006 | Bolduc et al. |
| 2006/0079943 A1 | 4/2006 | Narcisco, Jr. |
| 2006/0079950 A1 | 4/2006 | Lehnhardt et al. |
| 2006/0085041 A1 | 4/2006 | Hastings et al. |
| 2006/0085971 A1 | 4/2006 | Andrews et al. |
| 2006/0122522 A1 | 6/2006 | Chavan et al. |
| 2006/0161225 A1 | 7/2006 | Sormann et al. |
| 2006/0200030 A1 | 9/2006 | White et al. |
| 2006/0200031 A1 | 9/2006 | White et al. |
| 2006/0206163 A1 | 9/2006 | Wahlstrand et al. |
| 2006/0206165 A1 | 9/2006 | Jaax et al. |
| 2006/0206166 A1 | 9/2006 | Weiner |
| 2006/0217777 A1 | 9/2006 | Strom et al. |
| 2006/0222942 A1 | 10/2006 | Zhao et al. |
| 2006/0241733 A1 | 10/2006 | Zhang et al. |
| 2006/0241736 A1 | 10/2006 | Haldeman |
| 2006/0259088 A1 | 11/2006 | Pastore et al. |
| 2006/0271137 A1 | 11/2006 | Stanton-Hicks |
| 2006/0271166 A1 | 11/2006 | Thill et al. |
| 2006/0275659 A1 | 12/2006 | Kim et al. |
| 2006/0287700 A1 | 12/2006 | White et al. |
| 2006/0293741 A1 | 12/2006 | Johnson et al. |
| 2007/0027514 A1 | 2/2007 | Gerber |
| 2007/0027515 A1 | 2/2007 | Gerber |
| 2007/0043414 A1 | 2/2007 | Fifer et al. |
| 2007/0043424 A1 | 2/2007 | Pryor |
| 2007/0088396 A1 | 4/2007 | Jacobson |
| 2007/0088418 A1 | 4/2007 | Jacobson |
| 2007/0129637 A1 | 6/2007 | Wolinsky et al. |
| 2007/0150020 A1 | 6/2007 | Hokanson et al. |
| 2007/0154801 A1 | 7/2007 | Hyung et al. |
| 2007/0156126 A1 | 7/2007 | Flaherty et al. |
| 2007/0179552 A1 | 8/2007 | Dennis et al. |
| 2007/0179583 A1 | 8/2007 | Goetzinger et al. |
| 2007/0197939 A1 | 8/2007 | Wallace et al. |
| 2007/0247786 A1 | 10/2007 | Aamodt et al. |
| 2007/0255295 A1 | 11/2007 | Starkebaum et al. |
| 2007/0255383 A1 | 11/2007 | Gerber et al. |
| 2007/0260294 A1 | 11/2007 | Schulman et al. |
| 2007/0293909 A1 | 12/2007 | Cowan et al. |
| 2007/0293922 A1 | 12/2007 | Soltis et al. |
| 2007/0299492 A1 | 12/2007 | Zhang et al. |
| 2008/0004535 A1 | 1/2008 | Smits |
| 2008/0009750 A1 | 1/2008 | Aeby et al. |
| 2008/0051704 A1 | 2/2008 | Patel et al. |
| 2008/0071178 A1 | 3/2008 | Greenland et al. |
| 2008/0071248 A1 | 3/2008 | Delgado et al. |
| 2008/0103578 A1 | 5/2008 | Gerber |
| 2008/0132981 A1 | 6/2008 | Gerber |
| 2008/0132982 A1 | 6/2008 | Gerber |
| 2008/0148554 A1 | 6/2008 | Merrill et al. |
| 2008/0167702 A1 | 7/2008 | Ransbury et al. |
| 2008/0172118 A1 | 7/2008 | Johnson et al. |
| 2008/0183225 A1 | 7/2008 | Adamski et al. |
| 2008/0275350 A1 | 11/2008 | Liao et al. |
| 2008/0283066 A1 | 11/2008 | Delgado et al. |
| 2009/0018644 A1 | 1/2009 | Weber et al. |
| 2009/0105557 A1 | 4/2009 | Najafi et al. |
| 2009/0163969 A1 | 6/2009 | Donofrio |
| 2009/0177095 A1 | 7/2009 | Aeby et al. |
| 2009/0192514 A1 | 7/2009 | Feinberg et al. |
| 2009/0192585 A1 | 7/2009 | Bloom et al. |
| 2009/0234367 A1 | 9/2009 | Verma |
| 2009/0264991 A1 | 10/2009 | Paul et al. |
| 2009/0270741 A1 | 10/2009 | Vanney et al. |
| 2009/0275818 A1 | 11/2009 | Rau et al. |
| 2009/0281380 A1 | 11/2009 | Miller et al. |
| 2009/0299429 A1 | 12/2009 | Mayotte |
| 2009/0309273 A1 | 12/2009 | Parker |
| 2009/0326346 A1 | 12/2009 | Kracker et al. |
| 2010/0030063 A1 | 2/2010 | Lee et al. |
| 2010/0030321 A1 | 2/2010 | Mach |
| 2010/0063478 A1 | 3/2010 | Selkee |
| 2010/0082087 A1 | 4/2010 | Silipo et al. |
| 2010/0161027 A1 | 6/2010 | Orr |
| 2010/0179449 A1 | 7/2010 | Chow et al. |
| 2010/0179561 A1 | 7/2010 | Pilarski et al. |
| 2010/0256695 A1 | 10/2010 | Iyer et al. |
| 2010/0304209 A1 | 12/2010 | Lund et al. |
| 2010/0305628 A1 | 12/2010 | Lund et al. |
| 2010/0305629 A1 | 12/2010 | Lund et al. |
| 2010/0305636 A1 | 12/2010 | Lund et al. |
| 2010/0305653 A1 | 12/2010 | Lund et al. |
| 2011/0028852 A1 | 2/2011 | Alfoqaha |
| 2011/0029027 A1 | 2/2011 | Wengreen et al. |
| 2011/0029057 A1 | 2/2011 | Flach et al. |
| 2011/0190842 A1* | 8/2011 | Johnson ............... A61N 1/375 607/37 |
| 2011/0230923 A1 | 9/2011 | Swanson et al. |
| 2012/0108922 A1 | 5/2012 | Schell et al. |
| 2012/0108986 A1 | 5/2012 | Beasley et al. |
| 2012/0109002 A1 | 5/2012 | Mothilal et al. |
| 2012/0172891 A1 | 7/2012 | Lee |
| 2012/0172892 A1 | 7/2012 | Grubac et al. |
| 2012/0197349 A1 | 8/2012 | Griswold et al. |

FOREIGN PATENT DOCUMENTS

| | | |
|---|---|---|
| EP | 0928598 A2 | 8/2000 |
| EP | 1068836 A2 | 1/2001 |
| EP | 1488735 A1 | 12/2004 |
| WO | WO 8303348 A1 | 10/1983 |
| WO | WO 0013585 A1 | 3/2000 |

(56) References Cited

FOREIGN PATENT DOCUMENTS

| WO | WO 0016686 A2 | 3/2000 |
| WO | WO 0059376 A1 | 10/2000 |
| WO | WO 0187137 A2 | 11/2001 |
| WO | WO 0230295 A1 | 4/2002 |
| WO | WO 0254980 A2 | 7/2002 |
| WO | WO 2004068748 A1 | 8/2004 |
| WO | WO 2005028023 A1 | 3/2005 |
| WO | WO 2005067817 A1 | 7/2005 |
| WO | WO 2006062725 A1 | 6/2006 |
| WO | WO 2006124729 A2 | 11/2006 |
| WO | WO 2007022180 A1 | 2/2007 |
| WO | WO 2007028035 A1 | 3/2007 |
| WO | WO 2007047681 A2 | 4/2007 |
| WO | WO 2007057739 A1 | 5/2007 |
| WO | WO 2007082115 A2 | 7/2007 |
| WO | WO 2008057720 A1 | 5/2008 |
| WO | WO 2008060197 A1 | 5/2008 |
| WO | WO 2008144191 A2 | 11/2008 |
| WO | WO 2009039400 A1 | 3/2009 |
| WO | WO 2009120636 A1 | 10/2009 |
| WO | WO 2009124287 A1 | 10/2009 |

OTHER PUBLICATIONS

Luna Technologies, "About Distributed Sensing Technology" 2 pages (2010).

Wegmuller, "Intra-Body Communication for Biomedical Sensor Networks"; Dissertation submitted to ETH ZURICH; 2007; Diss. ETHD No. 17323; 161 pages.

U.S. Appl. No. 13/594,482, by Kamal Deep Mothilal et al., filed Aug. 24, 2012.

* cited by examiner

IMPLANTABLE MEDICAL DEVICE ELECTRODE ASSEMBLY

TECHNICAL FIELD

This disclosure relates to implantable medical device electrodes.

BACKGROUND

Various implantable medical devices (IMDs) may be used for therapeutically treating or monitoring one or more physiological conditions of a patient. Such IMDs may be adapted to monitor or treat conditions or functions relating to heart, blood vessels, muscle, nerve, brain, stomach, endocrine organs or other organs and their related functions. Advances in design and manufacture of miniaturized IMDs have resulted in IMDs capable of therapeutic as well as diagnostic functions, such as pacemakers, cardioverters, defibrillators, biochemical sensors, pressure sensors, various endovascular IMDs, and the like. Such IMDs may have electronic functions and may be wireless, with the ability to transmit data electronically either to another IMD implanted in the patient or to another device located externally of the patient, or both. IMDs with electronic functions may be coupled to electrical leads for delivering stimulation and sensing physiological parameters of the patient, catheters for delivering a substance, or may be leadless or catheterless. IMDs with electronic functions may include electrodes or sensors formed on, integral with, or within a housing of the IMD. Other IMDs may have purely mechanical and/or pharmaceutical functions, such as stents.

IMDs may include electrodes that provide one or more functions such as stimulation, sensing and/or other functionality. In various examples, an electrode may be distinct component of an IMD or a conductive housing of an IMD may also serve as an electrode. As another example, a conductive fixation mechanism for the IMD, such as a helical coil, may also serve as an electrode.

SUMMARY

In different examples, this disclosure describes leadless IMDs suitable for implantation within a vasculature within a patient. Such IMDs may include sensors. As one particular example, an IMD includes a pressure sensor and is configured for minimally invasive placement in a pulmonary artery of the patient.

As described herein, IMDs may include a conductive elongated body enclosing components of the IMD and an electrode mounted to one end of conductive elongated body. The electrode may be electrically isolated from the conductive elongated body with an insulator between the conductive elongated body and the electrode. In some examples, the insulator attaches to the body by way of a first snap-fit connection and the electrode attaches to the body and insulator by way of a second snap-fit connection. In this manner, such configurations as described herein may provide a strong mechanical connection between the body and the electrode while electrically isolating the electrode from the body.

In the same or different examples, an IMD may include a body containing components of the IMD, such as a sensor as well as a battery attached to the body. The battery may be in electrical communication with components within the body. The IMD may further include a fixation mechanism, for attaching the IMD to tissue of a patient. The fixation mechanism may be attached directly to the battery, but not directly to the body of the IMD. Such a configuration may avoid stressing the body from the attachment point of the fixation mechanism. As disclosed herein, such stress at the attachment point may cause inaccurate or imprecise sensor measurements. For this reason, such configurations may provide improved accuracy of sensor measurements as compared to similar devices with fixation mechanisms attached directly to a body of the IMD that encloses components including a sensor of the IMD.

In one example, this disclosure is directed to an implantable medical device comprising an electrode that forms a first snap-fit attachment area, and an insulator that forms a through-hole, a second snap-fit attachment area and a third snap-fit attachment area. The second snap-fit attachment area mates with the first snap-fit attachment area of the electrode. The implantable medical device further comprises a body including an elongated conductive housing and a feedthrough wire extending therefrom. The body forms a fourth snap-fit attachment area on one end that mates with the third snap-fit attachment area of the insulator such that the feedthrough wire extends through the through-hole of the insulator. The housing encloses at least one of a battery, a sensor, and an electronic circuit. The insulator functions to electrically isolate the electrode from the housing of the body In another example, this disclosure is directed to a method of assembling an implantable medical device. The implantable medical device includes an electrode that forms a first snap-fit attachment area, and an insulator that forms a through-hole, a second snap-fit attachment area and a third snap-fit attachment area. The second snap-fit attachment area is configured to mate with the first snap-fit attachment area of the electrode. The implantable medical device further includes a body including an elongated conductive housing and a feedthrough wire extending therefrom. The body forms a fourth snap-fit attachment area on one end that is configured to mate with the third snap-fit attachment area of the insulator. The housing encloses at least one of a battery, a sensor, and an electronic circuit. The method comprises securing the insulator to the body by mating the third snap-fit attachment area of the insulator with the fourth snap-fit attachment area of the body to form an assembly including the insulator and the body with the feedthrough wire extending through the through-hole of the insulator, and securing the electrode to the assembly including the insulator and the body by mating the first snap-fit attachment area of the electrode with the second snap-fit attachment area of the insulator. The insulator functions to electrically isolate the electrode from the housing of the body.

In a further example, this disclosure is directed to an implantable medical device comprising a body including an elongated conductive housing and a feedthrough wire extending therefrom. The housing encloses at least one of a battery, a sensor, and an electronic circuit. The implantable medical device further comprises an electrode in electrical contact with the feedthrough wire, and means for electrically isolating the electrode from the conductive housing of the body.

In an example, this disclosure is directed to an implantable medical device comprising a battery including a conductive battery case and a battery feedthrough extending therefrom, and a body including an elongated conductive housing, the housing being secured to the battery adjacent to the battery feedthrough. The implantable medical device further comprises components enclosed within the body, the components including a sensor configured to sense a physiological parameter of a patient, wherein the battery feedthrough is electrically connected to the components encased within the body. The implantable medical device further comprises a fixation member attached directly to an external surface of the conductive battery case and not directly attached to the housing.

In another example, this disclosure is directed to a method of assembling an implantable medical device. The implantable medical device includes a battery including a conductive battery case and a battery feedthrough extending therefrom, a body including an elongated conductive housing, and components enclosed within the body. The components include a sensor configured to sense a physiological parameter of a patient. The battery feedthrough is electrically connected to the components encased within the body. The implantable medical device further includes a fixation member attached directly to an external surface of the conductive battery case and not directly attached to the housing. The method comprises securing the housing of the body to the battery case adjacent to the battery feedthrough, and attaching the fixation member directly to an external surface of the battery case.

In a further example, this disclosure is directed to a implantable medical device comprising a battery including a conductive battery case and a battery feedthrough extending therefrom, a body including an elongated conductive housing, the housing being secured to the battery adjacent to the battery feedthrough, components enclosed within the body, the components including a sensor configured to sense a physiological parameter of a patient, a fixation member, and means for securing the fixation member to the implantable medical device without direct contact between the body and the fixation member.

DETAILED DESCRIPTION

Figure 1:
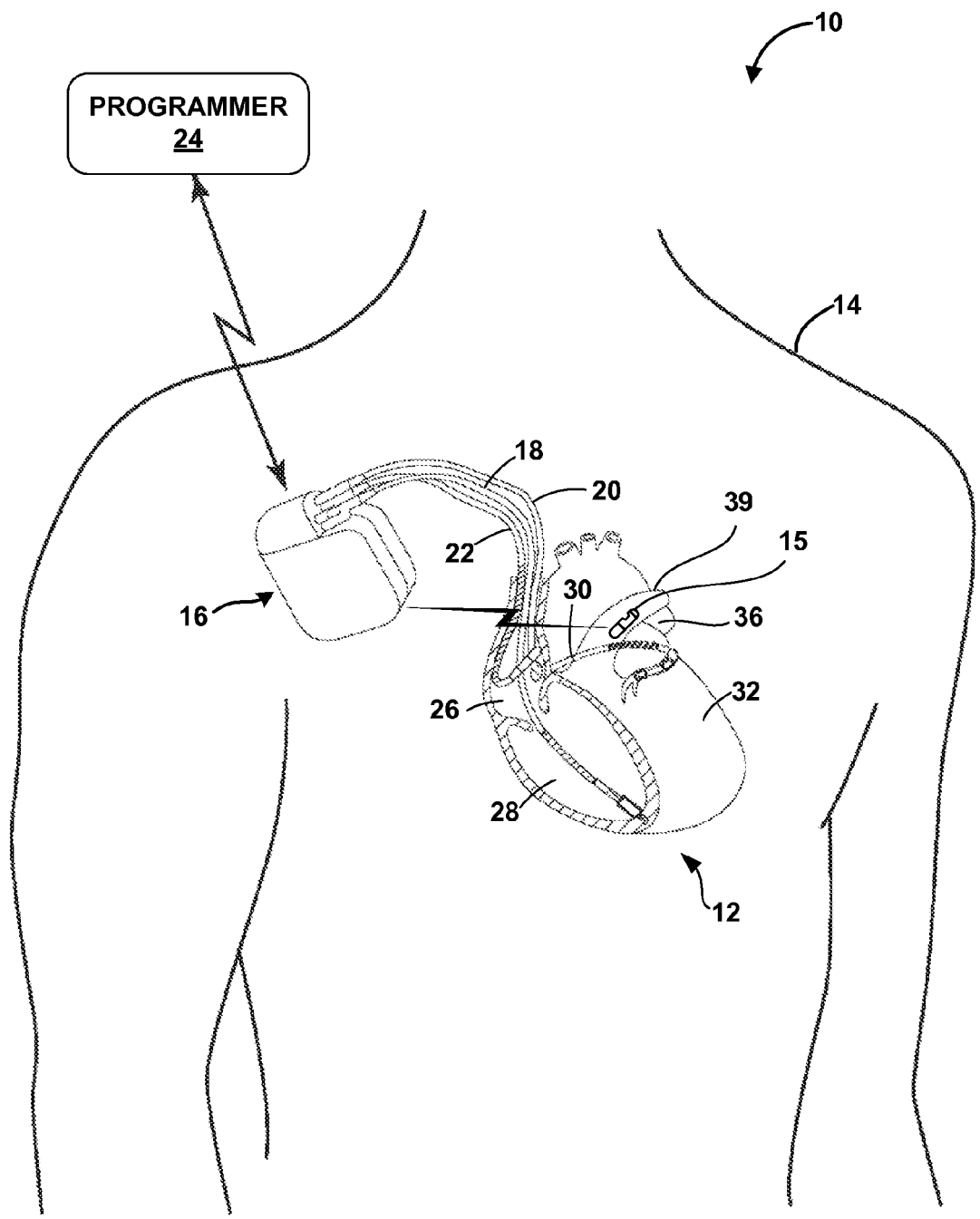
FIG. 1 is a conceptual drawing illustrating an example system that includes an implantable medical device (IMD) coupled to implantable medical leads and a leadless IMD including a sensor.

FIG. 1 is a conceptual diagram illustrating an example medical system 10 that may be used for sensing of physiological parameters of patient 14 and/or to provide therapy to heart 12 of patient 14. Medical system 10 includes an IMD 16, which is coupled to leads 18, 20, and 22, and programmer 24. IMD 16 may be, for example, an implantable pacemaker, cardioverter, and/or defibrillator that provide electrical signals to heart 12 via electrodes coupled to one or more of leads 18, 20, and 22. Patient 14 is ordinarily, but not necessarily, a human patient.

IMD 16 may include electronics and other internal components necessary or desirable for executing the functions associated with the device. In one example, IMD 16 includes one or more processors, memory, a signal generator, sensing module and telemetry modules, and a power source. In general, memory of IMD 16 may include computer-readable instructions that, when executed by a processor of the IMD, cause it to perform various functions attributed to the device herein. For example, a processor of IMD 16 may control the signal generator and sensing module according to instructions and/or data stored on memory to deliver therapy to patient 14 and perform other functions related to treating condition(s) of the patient with IMD 16.

The signal generator of IMD 16 may generate electrical stimulation that is delivered to patient 12 via electrode(s) on one or more of leads 18, 20, and 22, in order to provide, e.g., cardiac sensing, pacing signals, or cardioversion/defibrillation shocks.

The sensing module of IMD 16 may monitor electrical signals from electrode(s) on leads 18, 20, and 22 of IMD 16 in order to monitor electrical activity of heart 12, such as electrocardiogram depolarizations of heart 12. In one example, the sensing module may include a switch module to select which of the available electrodes on leads 18, 20, and 22 of IMD 16 are used to sense the heart activity. Additionally, the sensing module of IMD 16 may include multiple detection channels, each of which includes an amplifier, as well as an analog-to-digital converter for digitizing the signal received from a sensing channel for, e.g., electrogram signal processing by a processor of the IMD.

A telemetry module of IMD 16 may include any suitable hardware, firmware, software or any combination thereof for communicating with another device, such as programmer 24. Under the control of a processor of IMD 16, the telemetry module may receive downlink telemetry from and send uplink telemetry to programmer 24 with the aid of an antenna, which may be internal and/or external.

Leads 18, 20, 22 extend into the heart 12 of patient 14 to facilitate sensing of electrical activity of heart 12 and/or delivery of electrical stimulation to heart 12 by IMD 16, or to allow other sensors or transducers attached to the leads to make measurements. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., pulses with increasing energy levels, until a fibrillation of heart 12 is stopped. IMD 16 detects fibrillation employing any of a number of known fibrillation detection techniques.

System 10 may, in some examples, additionally or alternatively include one or more leads or lead segments (not shown in FIG. 1) that deploy one or more electrodes within the vena cava or other vein. These electrodes may allow alternative electrical sensing configurations that may provide improved or supplemental sensing in some patients. Furthermore, in some examples, physiological therapy/monitoring system 10 may include temporary or permanent epicardial or subcutaneous leads, instead of or in addition to leads 18, 20 and 22. Such leads may be used for one or more of cardiac sensing, pacing, or cardioversion/defibrillation.

Figure 3A:
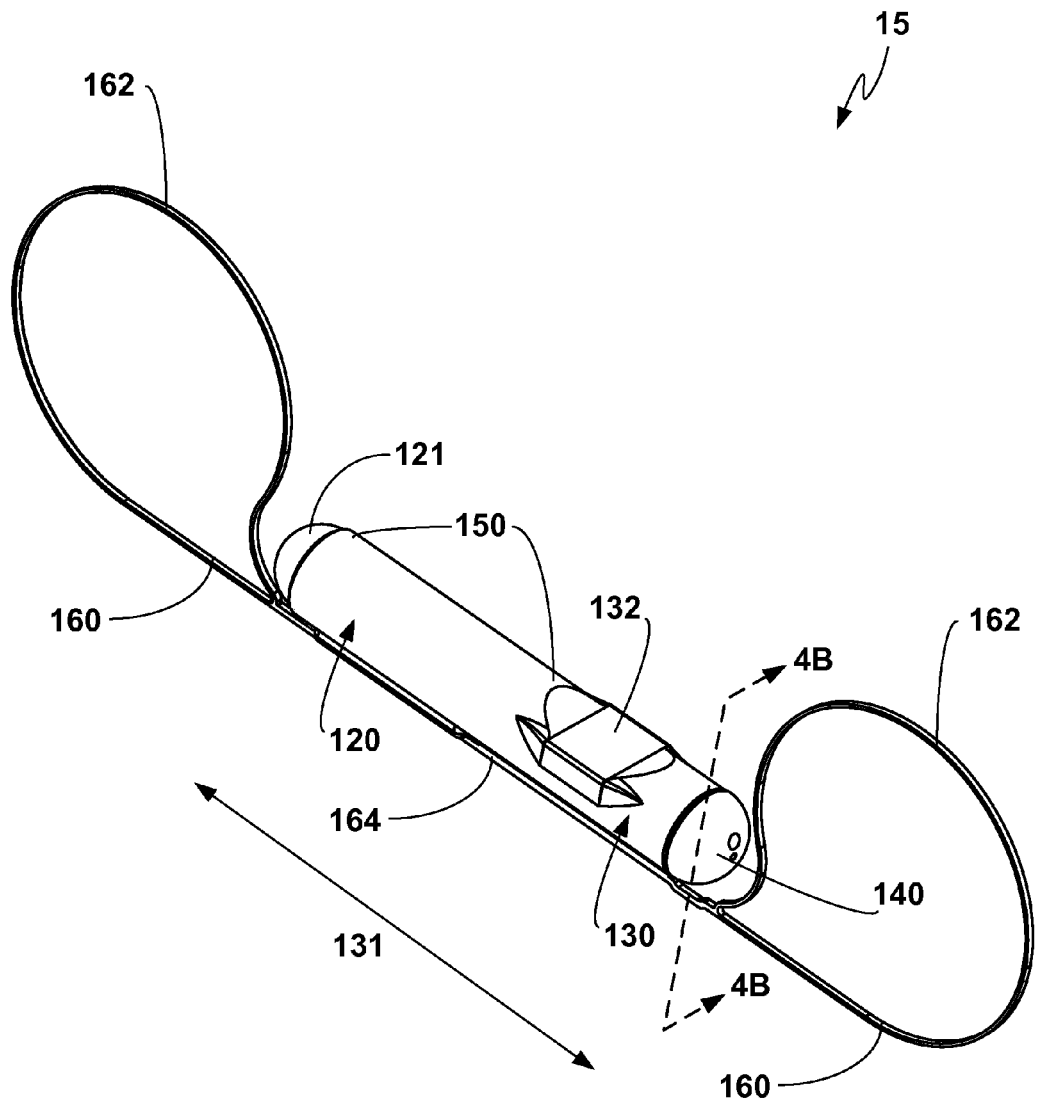
FIGS. 3A-3B illustrate the IMD of FIG. 1 in further detail.

System 10 also includes IMD 15, which includes a sensor 132 (FIG. 3A). In the illustrated example, IMD 15 is implanted in pulmonary artery 39. While shown within pulmonary artery 39 of patient 14, IMD 15 could be within a chamber of the heart, or generally within the circulatory system. In one example, IMD 15 is configured to sense blood pressure of patient 14. For example, IMD 15 may be arranged in pulmonary artery 39 and be configured to sense the pressure of blood flowing from the right ventricle outflow tract (RVOT) from right ventricle 28 through the pulmonary valve to pulmonary artery 39. IMD 15 may therefore directly measure the pulmonary artery diastolic pressure (PAD) of patient 14. The PAD value is a pressure value that can be employed in patient monitoring. For example, PAD may be used as a basis for evaluating congestive heart failure in a patient.

In other examples, however, IMD 15 may be employed to measure blood pressure values other than PAD. For example, IMD 15 may be arranged in right ventricle 28 of heart 14 to sense RV systolic or diastolic pressure. As shown in FIG. 1, IMD 15 is positioned in the main trunk of pulmonary artery 39. In other examples, a sensor, such as IMD 15 may be either positioned in the right or left pulmonary artery beyond the bifurcation of the pulmonary artery.

Moreover, the placement of IMD 15 is not restricted necessarily to the pulmonary side of the circulation. It could potentially be placed in the systemic side of the circulation—e.g., under certain conditions and with appropriate safety measures, it could even be placed in the left atrium, left ventricle, or aorta. Additionally, IMD 15 is not restricted to placement within the cardiovascular system. For example, the sensor might be placed in the renal circulation. IMD 15 placed in the renal circulation may be beneficial, for example, in circumstances in which IMD 16 is configured to treat heart failure based on some estimate of the degree of renal insufficiency in the patient derived from the monitoring of pressure or some other indication of renal circulation by the sensor. In this or other non-cardiovascular examples, the sensor may still communicate with IMD 16, or one or more sensors on leads 18, 20, or 22.

In some examples, IMD 15 includes a pressure sensor configured to respond to the absolute pressure inside pulmonary artery 39 of patient 14. IMD 15 may include, in such examples, any of a number of different types of pressure sensors. One form of pressure sensor that may be useful for measuring blood pressure is a capacitive pressure sensor. Another example pressure sensor is an inductive sensor. In some examples, IMD 15 may also comprise a piezoelectric or piezoresistive pressure transducer. In some examples, IMD 15 may comprise a flow sensor.

Figure 2:
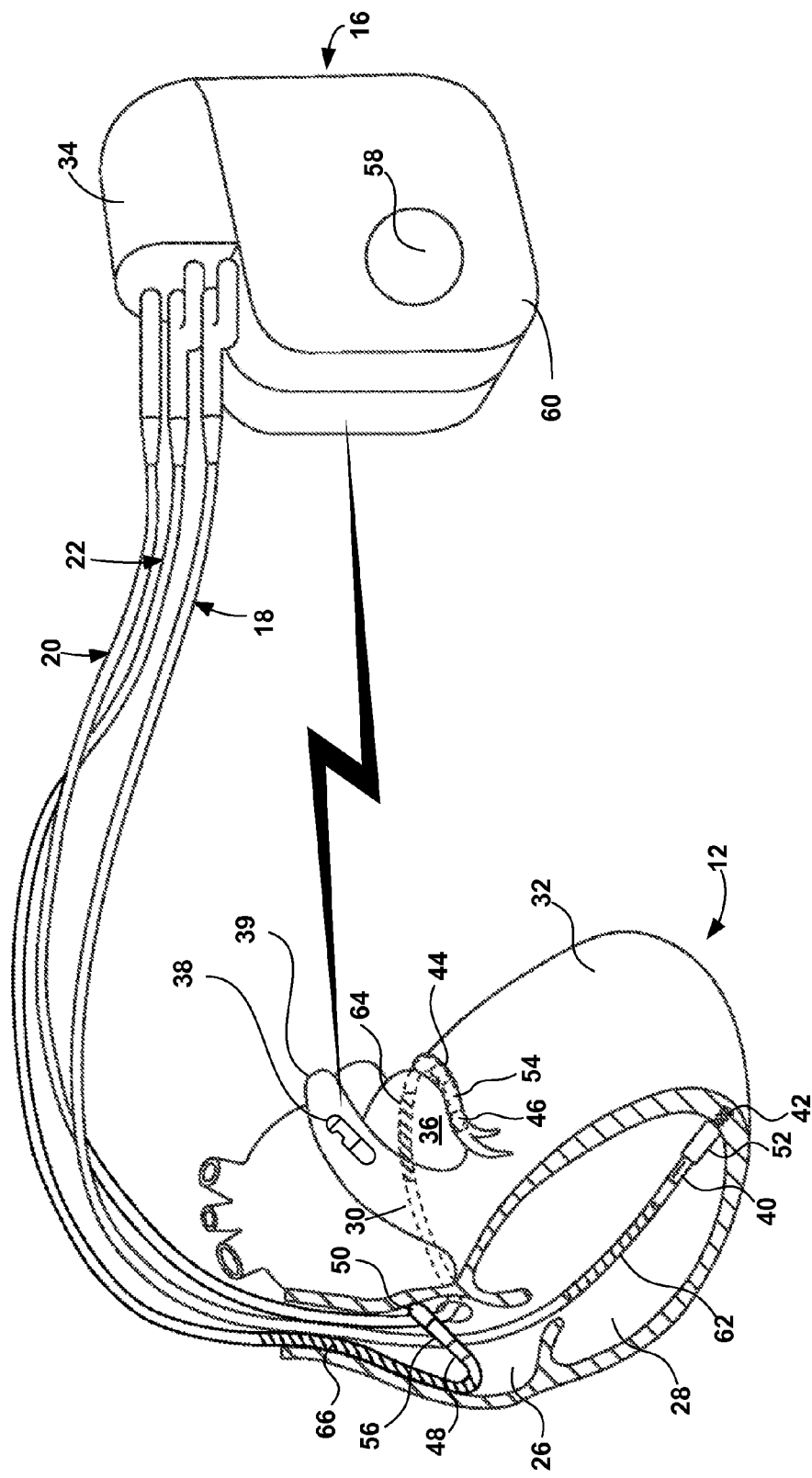
FIG. 2 is a conceptual drawing illustrating, in greater detail, the example IMD, leads, and sensor of FIG. 1 in conjunction with a heart.

In one example, IMD 15 comprises a leadless pressure sensor including capacitive pressure sensing elements configured to measure blood pressure within pulmonary artery 39. As illustrated in FIGS. 1 and 2, IMD 15 may be in wireless communication with IMD 16 or one or more sensors on leads 18, 20, or 22, e.g., in order to transmit blood pressure measurements to the IMD 16. IMD 15 may employ, e.g., radio frequency (RF) or other telemetry techniques for communicating with IMD 16 and other devices, including, e.g., programmer 24. In another example, IMD 15 may include a tissue conductance communication (TCC) system by which the device employs tissue of patient 14 as an electrical communication medium over which to send and receive information to and from IMD 16 and other devices.

In some examples, IMD 15 may be implanted within other body lumens, such as other vasculature of patient 14. Additionally or alternatively to including a pressure sensor, IMD 15 may also include sensors such as, but not limited to a cardiac electrogram or ECG sensor, a fluid flow sensor, an arterial, venous or tissue oxygen, $CO_2$, pH (acidity) sensor, a perfusion sensor, a hemoglobin sensor, an accelerometer (single or multi-axis), a glucose sensor, a potassium or similar plasma ion sensor, a temperature sensor and/or other sensors. In some examples, system 10 may include a plurality of leadless IMDs, e.g., to provide sensing of one or more physiological conditions of patient 14 at a variety of locations.

In some examples, IMD 16 may be solely a monitoring device, attached to various sensors, or even a monitoring device that only communicates with one or more devices 38 in various locations of the heart, or other vasculature, or even other organs. Such a device could be used, for example, to provide an integrated physiologic monitoring system that monitors, e.g., heart failure and one or more of its comorbidities (e.g. diabetes, renal function, etc.). Further, IMD 16 could be a combined monitoring and therapy system with multiple sensor and or "remote" therapy devices, 38. For example, IMD 16 could control a device, which may have similar outer housing dimensions, and may be implanted similarly to IMD 15, but which are configured to act as leadless pacemakers, in the right and left ventricles, (or on the left ventricular epicardium), as a means of providing cardiac resynchronization. IMD 16 could then also communicate with other sensors 38 in other vessels or organs, such as sensors of flow, pressure, or other parameters, for the purpose of additional monitoring and control of heart failure. Heart failure is rapidly becoming viewed as a multi-system disease, which may affect the heart, lungs, kidneys, and pancreatic function.

Programmer 24 shown in FIG. 1 may be a handheld computing device, computer workstation, or networked computing device. Programmer 24 may include electronics and other internal components necessary or desirable for executing the functions associated with the device. In one example, programmer 24 includes one or more processors and memory, as well as a user interface, telemetry module, and power source. In general, memory of programmer 24 may include computer-readable instructions that, when executed by a processor of the programmer, cause it to perform various functions attributed to the device herein. Memory, processor(s), telemetry, and power sources of programmer 24 may include similar types of components and capabilities described above with reference to similar components of IMD 16. The programmer may also be a dedicated wireless system that communicates with IMDs 15 and/or 16 remotely, say, from the patient's bedside table, while the patient sleeps.

In one example, programmer 24 includes a user interface that receives input from a user. The user interface may include, for example, a keypad and a display, which may be, for example, a cathode ray tube (CRT) display, a liquid crystal display (LCD) or light emitting diode (LED) display. The keypad may take the form of an alphanumeric keypad or a reduced set of keys associated with particular functions. Programmer 24 can, additionally or alternatively, include a peripheral pointing device, such as a mouse, via which a user may interact with the user interface. In some examples, a display of programmer 24 may include a touch screen display, and a user may interact with programmer 24 via the display. The user may also interact with programmer 24 remotely via a networked computing device. Or, the "programmer" may be a fully automated monitoring base station for use in the patient's home, with little or no capability for the user to provide input or programming of the implanted device. A physician could also log into the programmer 24 from a remote location via the internet, cell phone technology, or other satellite-based communication, and program the implanted device(s).

A user, such as a physician, technician, surgeon, electrophysiologist, or other clinician, may interact with programmer 24 to communicate with IMDs 15 and/or 16. For example, the user may interact with programmer 24 to retrieve physiological or diagnostic information from IMDs 15 and/or 16. A user may also interact with programmer 24 to program IMDs 15 and/or 16, e.g., select values for operational parameters of the IMD.

For example, the user may use programmer 24 to retrieve information from IMD 16 regarding the rhythm of heart 12, trends therein over time, arrhythmic episodes, or sensor trends). As another example, the user may use programmer 24 to retrieve information from IMDs 15 and/or 16 regarding other sensed physiological parameters of patient 14, such as intracardiac or intravascular pressure, activity, posture, respiration, or thoracic impedance. The sensed physiological parameters may be based on information received from IMD 15. As another example, the user may use programmer 24 to retrieve information from IMDs 15 and/or 16 regarding the performance or integrity of IMDs 15 and/or 16 or other components of system 10, such as leads 18, 20 and 22, or a power source of IMDs 15 and/or 16. In some examples, this information may be presented to the user as an alert.

The user may use programmer 24 to program a therapy progression, select electrodes used to deliver electrical stimulation to heart 12 (e.g., in the form of pacing pulses or cardioversion or defibrillation shocks), select waveforms for the electrical stimulation, or select or configure a fibrillation detection algorithm for IMD 16. The user may also use programmer 24 to program aspects of other therapies provided by IMD 16, such as cardioversion or pacing therapies. In some examples, the user may activate certain features of IMD 16 by entering a single command via programmer 24, such as depression of a single key or combination of keys of a keypad or a single point-and-select action with a pointing device.

IMDs 15 and/or 16 and programmer 24 may communicate via wireless communication, e.g. via telemetry modules in each of the devices using any number of known techniques. Examples of communication techniques may include, for example, low frequency or RF telemetry, but other techniques are also contemplated. In some examples, programmer 24 may include a programming head that may be placed proximate to the patient's body near the IMD implant site in order to improve the quality or security of communication between the IMD and programmer 24.

In some examples, programmer 24 may communicate directly with both IMDs 15 and 16. In other examples, programmer 24 may communicate with IMD 16, which in turn may communicate with IMD 15, e.g., to control the function of IMD 15 and/or to retrieve patient physiological or device performance data from IMD 15. In some examples, data retrieved from IMD 15 may be used by IMD 16 to augment or control its therapy delivery and/or sensing functions, and/or may be transmitted to programmer 24 for user consideration. Commands from programmer 24 may be communicated to IMD 15 via IMD 16, in some examples. Other example medical systems need not have IMD 16 or provide therapy. For example, a medical system may only include IMD 15, which may communicate directly with an external device, e.g., programmer 24.

FIG. 2 is a conceptual diagram illustrating IMD 16 and leads 18, 20 and 22 of medical system 10 in greater detail. Leads 18, 20, 22 may be electrically coupled to a signal generator, e.g., stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of setscrews, connection pins, snap connectors, or another suitable mechanical coupling mechanism. Leads 18, 20 22 include electrodes for delivery of stimulation and/or sensing and may additionally include one or more sensors as mentioned above with respect to FIG. 1.

Each of the leads 18, 20, 22 includes an elongated insulative lead body, which may carry a number of concentric coiled conductors separated from one another by tubular insulative sheaths. Other lead configurations may also be used. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other examples, one or more of electrodes 42, 46 and 50 may take the form of small circular electrodes at the tip of a tined lead or other fixation member. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. The sensed electrical signals may be processed as a cardiac electrogram (EGM) signal by IMD 16.

Any combination of electrodes 40, 42, 44, 46, 48, 50, 58, 62, 64 and 66 may be considered a sensing configuration that has one or more electrodes. In some examples, a sensing configuration may be a bipolar electrode combination on the same lead, such as electrodes 40 and 42 of lead 18. In any sensing configuration, the polarity of each electrode in the sensing configuration may be configured as appropriate for the application of the sensing configuration.

In some examples, IMD 16 delivers pacing pulses via bipolar combinations of electrodes 40, 42, 44, 46, 48 and 50 to cause depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver cardioversion or defibrillation pulses to heart 12 via any combination of elongated electrodes 62, 64, 66, and housing electrode 58. Electrodes 58, 62, 64, 66 may also be used to deliver cardioversion pulses, e.g., a responsive therapeutic shock, to heart 12. Electrodes 62, 64, 66 may be fabricated from any suitable electrically conductive material, such as, but not limited to, platinum, platinum alloy or other materials known to be usable in implantable defibrillation electrodes.

The configuration of medical system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. As another example, other examples of therapy systems may include a single lead that extends from IMD 16 into right atrium 26 or right ventricle 28, or two leads that extend into a respective one of the right ventricle 26 and right atrium 26.

Figure 3B:
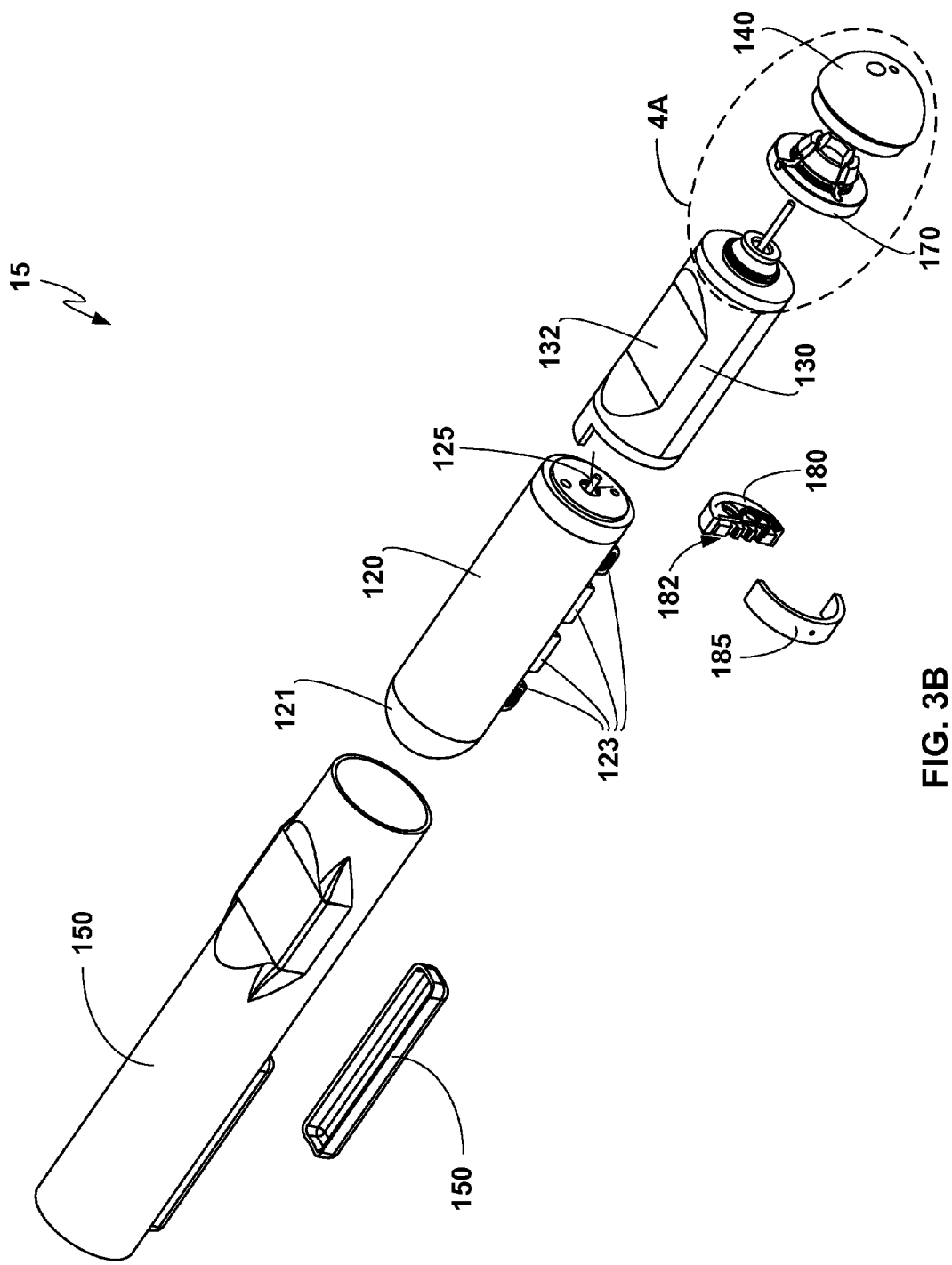

FIGS. 3A-3B illustrate IMD 15, which is configured for minimally invasive placement in a patient's blood vessel, e.g., as shown in FIG. 1. Specifically, FIG. 3A illustrates a perspective view of IMD 15, whereas FIG. 3B illustrates an exploded view of IMD 15. As shown in FIG. 3B, IMD 15 includes an elongated body 130 with sensor 132 and an elongated battery 120 in alignment with body 130. Electrode 140 is secured to the housing of body 130 on an opposite end of the housing relative to battery 120. Details of electrode 140 and insulator 170, which separates electrode 140 from the housing of body 130 are disclosed in further detail with respect to FIGS. 4A-4B. IMD 15 further includes fixation member 160, which is secured to the battery case of battery 120. Additionally, insulative overlay 150 covers portions of the housing of body 130 and the battery case of battery 120. As shown in FIG. 3B, insulative overlay 150 may comprise one or more components. In the specific example shown in FIG. 3B, insulative overlay 150 includes a separate component covering tabs 123 in addition to a tubular portion that battery 120 except for exposed end 121 and also covers all of body 130.

Electronic components of IMD 15, including sensor 132 are enclosed within body 130. As examples, the components may include an electronic circuit as well as a sensor. In different examples, IMD 15 may include any combination of the following sensors: a pressure sensor, a cardiac electrogram or ECG sensor, a fluid flow sensor, an oxygen, $CO_2$, pH or perfusion sensor, an accelerometer (single or multi-axis), a glucose sensor, a potassium or similar plasma ion sensor, a temperature sensor and/or other sensor.

Battery 120 includes a conductive battery case with battery feedthrough 125 extending therefrom into body 130. Likewise, body 130 includes an elongated conductive housing that is secured to battery 120 adjacent to battery feedthrough 125. Components, such as a sensor and other electronics are enclosed within the elongated conductive housing of body 130 and electrically connected to battery 125 via battery feedthrough 125. As shown in FIG. 3A, the battery case of battery 120 includes an exposed end 121 that extends beyond insulative overlay 150. Exposed end 121 may combine with electrode 140 to provide tissue conductance communication (TCC) between IMD 15 and a remote device, such as IMD 16 (FIG. 1). In other examples, exposed end 121 and/or electrode 140 may additionally or alternatively be used as electrodes for electrical sensing and/or stimulation functions of IMD 15.

In the example configuration shown in FIG. 3B, IMD 15 includes weld bar 180, with grooves 182. Grooves 182 are configured to receive battery feedthrough 125 and a corresponding wire (not shown) from body 130. Once battery 120, body 130 and weld bar 180 are placed in alignment with the feedthroughs within grooves 182 of weld bar 180, the feedthroughs are welded, e.g., via laser welding, to weld bar 180 to electrically connect battery 120 to components encased within the housing of body 130. An insulator is located between weld bar 180 and the battery case and the housing of body 130. Then the battery case of battery 120 may be welded to the housing of body 130. In the example of FIG. 3B, IMD 15 further includes seal ring 185, which may be combined with the battery case of battery 120 and the housing of body 130 to fully enclose weld bar 180, battery feedthrough 125 and a corresponding wire (not shown) from body 130. As an example, seal ring 185 may be formed from the same material as one or both of the battery case of battery 120 and the housing of body 130. The battery case of battery 120, the housing of body 130 and seal ring 185 may be welded to each other to form weld joint providing a hermetic seal that surrounds weld bar 180 and connecting the battery case of battery 120, the housing of body 130 and seal ring 185. In the example where battery 120 has a case negative configuration, the housing of body 130 maintains the same potential as the case of battery 120 such that no further connection is required between battery 120 and the components within the housing of body 130, i.e., the battery feedthrough 125 serves as one battery terminal and the case of battery 120 serves as another battery terminal to connect battery 120 to components within body 130.

IMD 15 further includes fixation member 160 attached directly to an external surface of the conductive battery case of battery 120 and not directly attached to the housing of body 130. Fixation member 160 is collapsible to a low profile to enable IMD 15 to be carried by a delivery catheter and navigated to a deployment site where it can be released. Upon release, fixation member 160 expands from a low profile configuration to an expanded configuration adapted to engage the walls of a vasculature to maintain the position of IMD 15 within the vasculature. As noted above, the term vasculature as referred to herein includes the heart itself such as heart ventricles and heart atriums. Fixation member 160 is attached to battery 120, and thereby body 130, in a manner such that when fixation member 160 is placed, body 130 is positioned against the wall of the vascular lumen such that sensing element 132 of body 130 is oriented away from the wall of the vascular lumen to be fully exposed to the blood in the vessel, without obstruction from the vessel wall. Spacing body 130 against the wall of the vascular lumen may minimize adverse obstruction to blood flow through the lumen.

Both the conductive battery housing of battery 120 and the elongated conductive housing of body 130 provide a substantially cylindrical shape. The conductive battery housing of battery 120 combines with the elongated conductive housing of body 130 to form an elongate, cylindrical shape with rounded ends and a cylindrical sidewall extending between the ends. This shape is considered to present low resistance to blood flow. Other housing configurations may be employed, however. The conductive battery housing of battery 120 and the elongated conductive housing of body 130 are formed from a biocompatible material that can be hermetically sealed when the battery 120 and body 130 are joined. A number of such biocompatible materials may be employed, as will be understood by those familiar with the art, including metals. For example, the conductive battery housing of battery 120 and the elongated conductive housing of body 130 may be formed from unalloyed titanium with an American Society for Testing and Materials (ASTM) grade 1, grade 2, grade 11 to grade 14, grade 23 or an alloyed titanium (grade 15) that includes aluminum and vanadium. Numerous other materials are also suitable. For examples in which the conductive battery housing of battery 120 and the elongated conductive housing of body 130 are metal, the metal should have sufficient malleability to facilitate secure attachment of the battery case of battery 120 to the fixation member 160 by crimping, as described in more detail below.

In examples where the battery case of battery 120, the housing of body 130 and fixation member 160 are conductive, the battery case of battery 120, the housing of body 130 and fixation member 160 will be at a common electrical potential. In some such examples, battery 120 may have a case-negative configuration. The conductive battery housing of battery 120 and the elongated conductive housing of body 130 may be encapsulated in insulative overlay 150 such as a biologically inert dielectric barrier material such as a film of silicone or polyp-xylylene) polymer sold under the trademark PARYLENE. In addition, all or a portion of fixation member 160 may also be encapsulated in an insulative coating such as a biologically inert dielectric barrier material such as a film of silicone or polyp-xylylene) polymer sold under the trademark PARYLENE.

Those portions of the housing or fixation member that are intended to serve a poles for intra-body wireless communication (e.g., to transmit or receive RF signals with a remote device such as IMD 16) may remain uncovered. Intra-body wireless communication may also be referred to as tissue conduction communication (TCC). In particular, exposed end 121 of the conductive battery housing of battery 120 may serve as a one pole for intra-body wireless communication whereas electrode 140 may serve as another pole. In some examples, a portion of fixation member 160 adjacent to exposed end 121 of the conductive battery housing of battery 120 may remain uncovered and combine with exposed end 121 of the conductive battery housing of battery 120 to form a single pole. In other examples, exposed end 121 of the conductive battery housing of battery 120 may be the only portion of IMD 15 serving as a pole opposite electrode 140.

In either example, insulative overlay 150 covering portions of the conductive battery housing of battery 120 and the elongated conductive housing of body 130 and the insulative coating covering all or a portion of fixation member 160 combine to increase the minimum distance between exposed surfaces of the conductive battery housing of battery 120 and fixation member 160 relative to electrode 140. As an example, the minimum distance between the exposed surfaces of the conductive battery housing of battery 120 and fixation member 160 and of electrode 140 may be no less than half of the length of IMD 15, not including fixation member 160, as measured along the largest major dimension 131 of IMD 15.

Fixation member 160 is wire-like and is configured to lie substantially in a single plane. In one example, fixation member 160 may be formed from a highly elastic, biocompatible alloy capable of forming stress induced martensite (SIM). Nitinol (TiNi) is an example of shape memory alloy materials that are also referred to as being "pseudoelastic" or "superelastic." Fixation member 160 shown includes a pair of longitudinally spaced oval loops 162 connected by an elongate linear attachment strut 164. In different examples, oval loops 162 may have a circular or an oblong shape. The loops 162 are spaced apart sufficiently to receive and embrace the battery 120/body 130 assembly extending lengthwise along attachment strut 164. The fixation member 160, including the attachment strut 164 may be formed from a sheet of material by laser cutting or electrochemical etching or other fabricating techniques known in the art. The resulting fixation member 160 has a substantially uniform thickness and is formed as a single, integral piece. The wire-like elements that make up the loops 162 and the attachment strut 164 may have a circular cross-section, or a non-circular cross section that may be square or rectangular.

The arrangement for attaching battery 120 to the strut 164 includes several pairs of plastically deformable tabs 123 that provide a means for securing the fixation member to IMD 15 without direct contact between body 130 and fixation member 160. In another example, a simple tube or weld joint may be used to secure fixation member 160 to battery 120.

Plastically deformable tabs 123 are formed integrally with the conductive battery case of battery 120 and at a location that is diametrically opposite the sensing element 132. The pairs of tabs 123 are aligned longitudinally and cooperate to define a longitudinally extending channel that is non-circular in cross-sectional shape (preferably rectangular) and is receptive to attachment strut 164 of the fixation member 160. At least one of the tabs 123 includes a portion protruding beyond attachment strut 164 when attachment strut 164 is contained in the channel. Attachment strut 164 is located transversely into the channel and the protruding tab portion is plastically deformed to overlie the strut to secure the battery case to the fixation member. The width of the longitudinally extending channel is selected to receive the rectangular cross section of attachment strut 164 in a snug fit to prevent the battery 120/body 130 assembly from rotating about the axis of attachment strut 164. Attachment of a fixation element to an IMD housing plastically deformable tabs is described in further detail in US Pat. Pub. No. 2012/0108922, titled "Implantable Medical Sensor and Fixation System" by Schell et al., the entire contents of which are incorporated by reference herein.

In other examples, fixation member 160 may be attached to the conductive battery case of battery 120 by way of deformable tubes secured to the conductive battery case as disclosed by US Pat. Pub. No. 2012/0109002, titled "Medical Device Fixation Attachment Mechanism" by Mothilal et al., the entire contents of which are incorporated by reference herein.

Figure 4A:
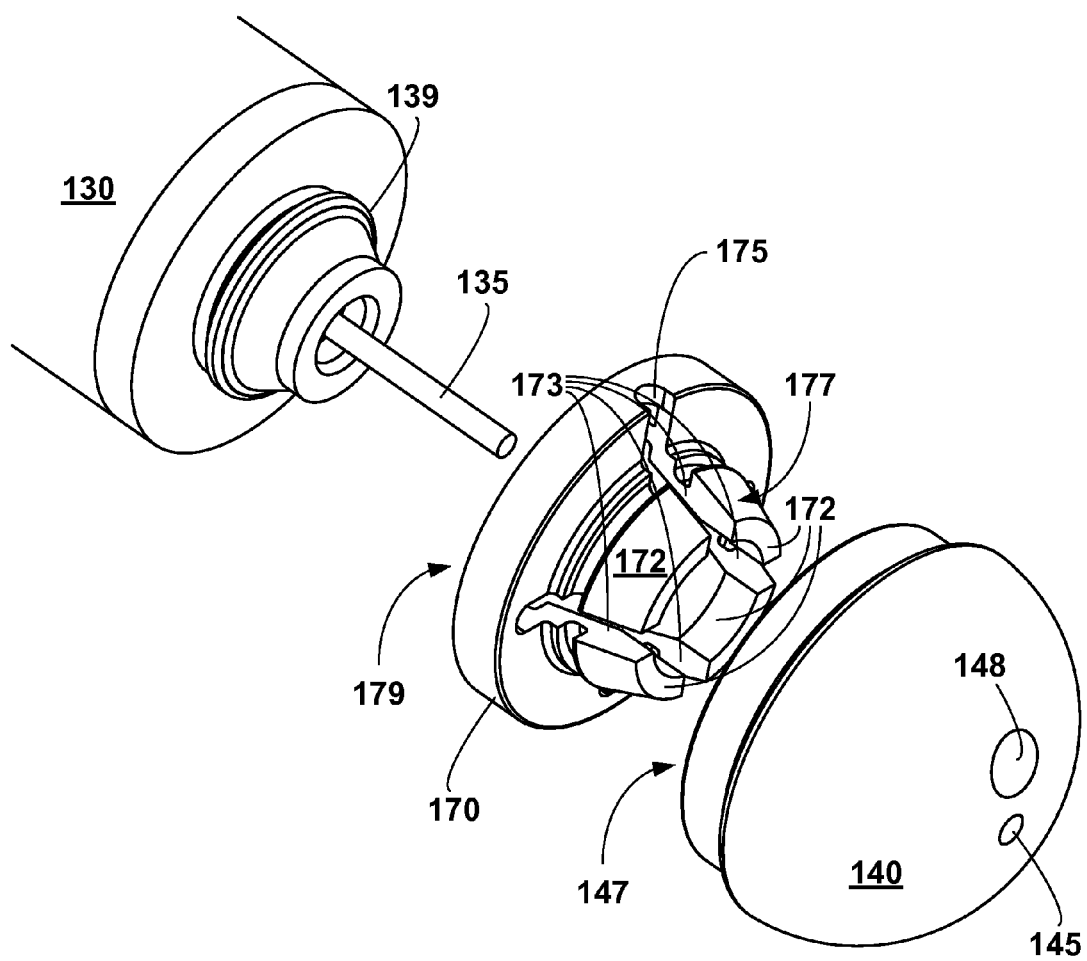
FIGS. 4A-4B illustrate the electrode assembly of the IMD of FIG. 1 in further detail.
Figure 4B:
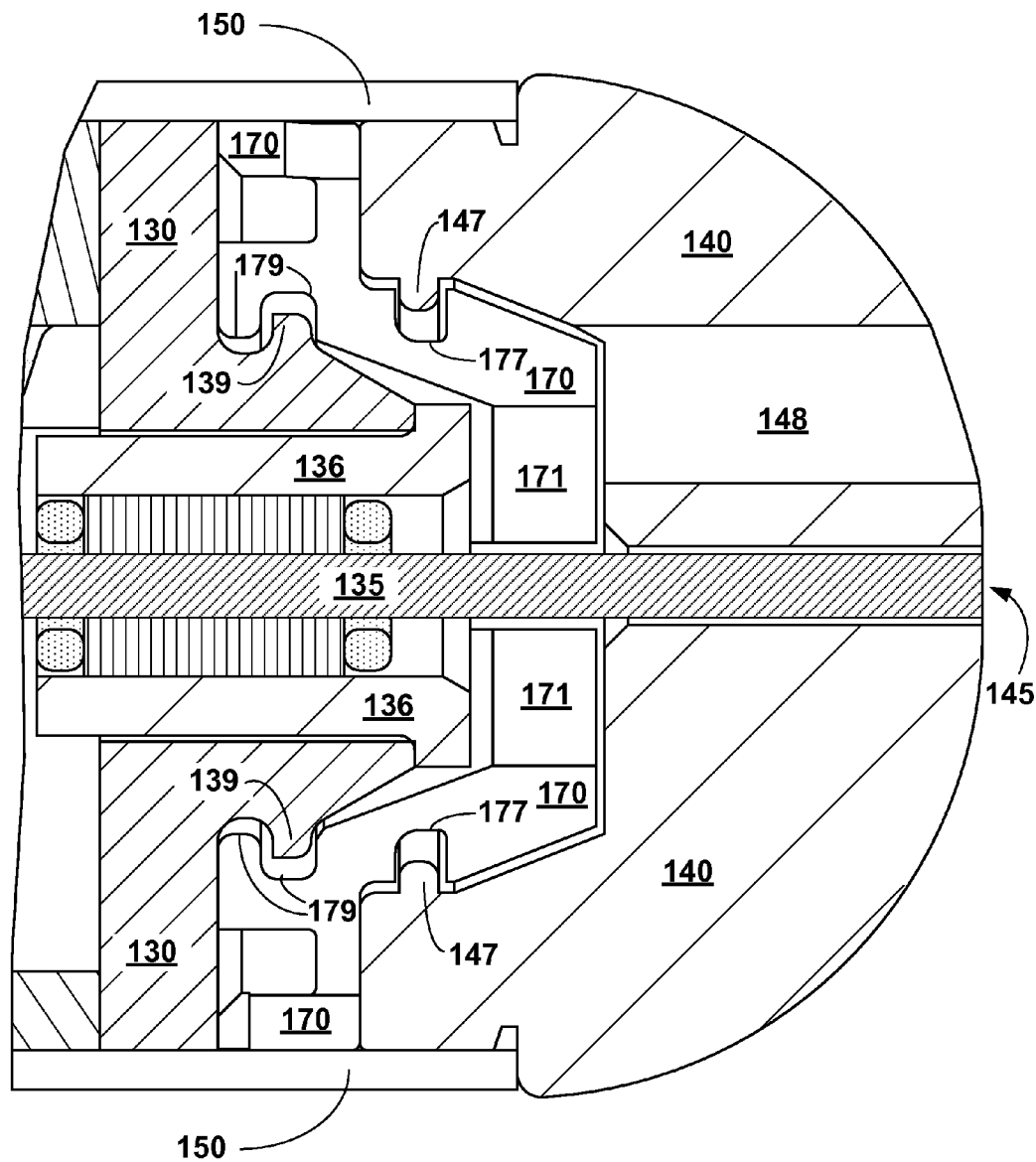

FIGS. 4A-4B illustrate the electrode assembly of IMD 15 in further detail. Specifically, FIG. 4A illustrates an exploded view of the electrode assembly of IMD 15 as indicated in FIG. 3B, whereas FIG. 4B illustrates a sectional of the electrode assembly of IMD 15 as indicated in FIG. 3A.

As shown in FIG. 4A, electrode 140 is secured to an end of body 130 that includes feedthrough wire 135. Feedthrough wire 135 provides an electrical connection between components enclosed within body 130 and electrode 140. Insulator 170 separates electrode 140 from the conductive housing of body 130 to electrically isolate electrode 140 from the conductive housing of body 130. Insulator 170 is formed from an electrically insulative biocompatible material, such as a polymeric material. In one example, insulator 170 may be formed from a thermoplastic such as polyether ether ketone (PEEK) polymer.

Feedthrough wire 135 of body 130 extends within feedthrough ferrule 136 (FIG. 4B). Body 130 further forms snap-fit attachment area 139 surrounding feedthrough ferrule 136. Likewise, insulator 170 forms snap-fit attachment area 179, which mates to snap-fit attachment area 139 of body 130. Insulator 170 also forms snap-fit attachment area 177, which mates to snap-fit attachment area 147 of electrode 140. As shown in FIG. 4B, the distal end of feedthrough ferrule 136 extends within the cavity forming snap-fit attachment area 147 of electrode 140, even though body 130 including feedthrough ferrule 136 is electrically isolated from electrode 140 by insulator 170. Locating the distal end of feedthrough ferrule 136 within the cavity forming snap-fit attachment area 147 of electrode 140 helps minimize the overall length of IMD 15.

In some examples, snap-fit attachment area 139 of body 130 may include a protrusion that is received by a recess of snap-fit attachment area 179 of insulator 170. Similarly, snap-fit attachment area 177 of insulator 170 may include a protrusion that is received by a recess of snap-fit attachment area 147 of electrode 140. In addition, each of the snap-fit attachment areas provides a consistent circumferential profile such that body 130, insulator 170 and electrode 140 can be attached at an angle so long as the mating snap-fit attachment areas are in axial alignment. However, these particular features are merely examples, and other snap-fit configurations may also be used within the spirit of this disclosure.

Insulator 170 forms through-hole 171 (FIG. 4B), through which feedthrough wire 135 passes to reach electrode 140. Electrode 140 forms hole 145 that receives feedthrough wire 135. In some examples, feedthrough wire 135 may be laser welded to electrode 140 to form a weld joint between feedthrough wire 135 and electrode 140 at hole 145.

Electrode 140 further forms hole 148, which receives an injection of an adhesive during the manufacture of IMD 15. The adhesive fills cavities between electrode 140, insulator 170 and body 130 to secure electrode 140 to body 130. Insulator 170 forms features that facilitate flow of the adhesive. In particular, insulator 170 includes tabs 172, which are separated by relief slots 173. Insulator 170 also forms an adhesive outlet 175 (FIG. 4A) that allows air to vacate the cavities between electrode 140, insulator 170 and body 130 during the filling of the cavities with the adhesive. In addition, excess adhesive may also flow from adhesive outlet 175 during the filling of the cavities with the adhesive. Numerous adhesives may be suitable for this application including medical adhesives such as Med 1137 and Med 2000 from NuSil Technology LLC of Santa Barbara, Calif., United States.

Figure 5:
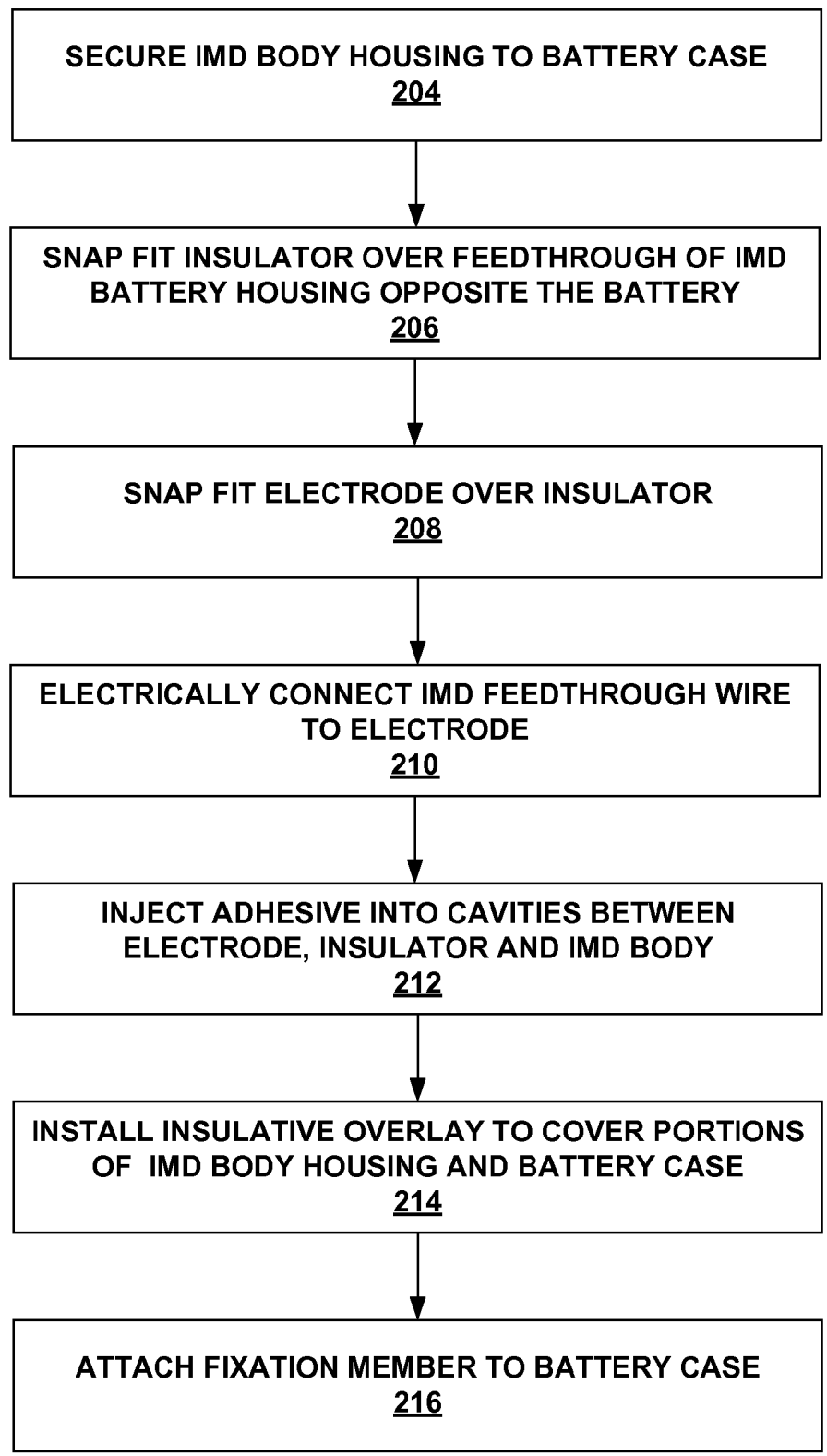
FIG. 5 is a flowchart illustrating example techniques for the manufacture of a leadless IMD, such as the leadless IMD including a sensor of FIG. 1.

FIG. 5 is a flowchart illustrating example techniques for the manufacture of a leadless IMD. For clarity, the techniques of FIG. 5 are discussed with respect to IMD 15; however, the techniques of FIG. 5 are not limited to IMD 15.

the example method of FIG. 5 further includes securing the housing of body 130 to the battery case of battery 120 adjacent to battery feedthrough 125 (204). As an example, securing the housing of body 130 to the battery case of battery 120 adjacent to battery feedthrough 125 may include welding the housing of body 130 to the battery case of battery 120 to form a weld joint between the housing of body 130 and the battery case of battery 120.

Steps 206 through 212 represent techniques used to mechanically and electrically connect electrode 140 to body 130. In practice, steps 206 through 212, techniques used to mechanically and electrically connect electrode 140 to body 130, may be performed before or after steps 202 through 204, techniques used to assemble battery 120, body 130 and fixation member 160.

According to the example method, insulator 170 is secured to body 130 by mating snap-fit attachment area 170 of insulator 170 with snap-fit attachment area 130 of body 130 to form an assembly including insulator 170 and body 130 with feedthrough wire 135 extending through through-hole 171 of insulator 170 (206). Next, electrode 140 is secured to the assembly including insulator 170 and body 130 by mating snap-fit attachment area 147 of electrode 140 with snap-fit attachment area 177 of insulator 170 (208). In this manner, insulator 170 functions to electrically isolate electrode 140 from the housing of body 130.

Electrode 140 is electrically connected to feedthrough wire 135 (210). For example, feedthrough wire 135 may be laser welded to electrode 140 to form a weld joint between feedthrough wire 135 and electrode 140 at hole 145.

Once insulator 170 is snap-fit to body 130 and electrode is snap-fit to the assembly including insulator 170 and body 130, an adhesive is injected into hole 148 to fill cavities between electrode 140, insulator 170 and body 130 (212). The adhesive flows from hole 140 into the cavities, which include relief slots 173 between tabs 172 of insulator 170. Once the cavities between electrode 140, insulator 170 and body 130 are filled with adhesive, excess adhesive may also flow from adhesive outlet 175. The adhesive functions further secure electrode 140 to body 130. In this manner, the combination of the snap-fit connections between body 130 and electrode 140 and between electrode 140 and insulator 170 combine with the adhesive to provide a strong mechanical connection between body 130 and electrode 140 while electrically isolating electrode 140 from body 130.

Insulative overlay 150 may be installed to cover portions of the housing of body 130 and the battery case of battery 120 (214). According to the example of FIG. 5, fixation member 160 is then directly attached to an external surface of the battery case of battery 120 (216). In some examples, attaching fixation member 160 directly to the external surface of the battery case of battery 120 may include positioning attachment strut 164 within a channel formed by plastically deformable tabs 123, and plastically deforming the protruding tab portion of plastically deformable tabs 123 to overlie strut 164 to secure the battery case of battery 120 to fixation member 160. At least one of plastically deformable tabs 123 protrudes beyond strut 164 when strut 164 is contained in the channel.

Notably, fixation member 160 is attached to the battery case of battery 120. This may alleviate stress on body 130 during the attachment of fixation member 160 to the battery case of battery 120. Such stress at the attachment point may cause inaccurate or imprecise sensor measurements by sensor 132 within body 130. By attaching fixation member 160 to the battery case of battery 120, stress on body 130 may be mitigated, which may improve the accuracy and precision of observations by sensor 132.

Various examples of this disclosure have been described. These and other examples are within the scope of the following claims.

What is claimed is:
1. An implantable medical device comprising:
an electrode that forms a first snap-fit attachment area;
an insulator that forms a through-hole, a second snap-fit attachment area and a third snap-fit attachment area, wherein the second snap-fit attachment area mates with the first snap-fit attachment area of the electrode; and
a body including an elongated conductive housing and a feedthrough wire extending therefrom, wherein the body forms a fourth snap-fit attachment area on one end that mates with the third snap-fit attachment area of the insulator such that the feedthrough wire extends through the through-hole of the insulator,
wherein the housing encloses at least one of a battery, a sensor, or an electronic circuit, and
wherein the insulator functions to electrically isolate the electrode from the housing of the body.

2. The implantable medical device of claim 1,
wherein the electrode forms a first hole that receives the feedthrough wire of the body, and
wherein the electrode forms a second hole that receives an injection of an adhesive, the implantable medical device further comprising the adhesive.

3. The implantable medical device of claim 2, wherein the adhesive fills cavities between the electrode, the insulator and the body to secure the electrode to the body.

4. The implantable medical device of claim 2, wherein the insulator forms cavities to receive the injection of the adhesive via the second hole of the electrode.

5. The implantable medical device of claim 1, further comprising a weld joint between the feedthrough wire and the electrode.

6. The implantable medical device of claim 1, wherein the housing of the body has a substantially cylindrical shape.

7. The implantable medical device of claim 1, wherein the sensor is a pressure sensor, wherein the housing encloses the pressure sensor and the electronic circuit.

8. The implantable medical device of claim 1,
wherein the housing encloses at least one of the sensor and the electronic circuit, and
wherein the implantable medical device further includes the battery connected to the body on an opposite end of the housing relative to the electrode.

9. The implantable medical device of claim 8, wherein the battery includes a battery feedthrough serving as a battery terminal for the battery, wherein the battery feedthrough is electrically connected to the components enclosed within the housing.

10. The implantable medical device of claim 9, wherein the battery terminal is a first battery terminal, wherein the battery includes a conductive battery case serving as a second battery terminal of the battery, wherein battery case is electrically and mechanically coupled to the housing of the body.

11. The implantable medical device of claim 1, wherein the implantable medical device includes the sensor, wherein the sensor selected from a group consisting of:
a pressure sensor;
a cardiac electrogram sensor;
an ECG sensor
a fluid flow sensor;
perfusion sensor
an oxygen sensor;
a carbon dioxide sensor;
an acidity sensor;
an accelerometer;
a glucose sensor;
a blood plasma sensor;
a potassium sensor; and
a temperature sensor.

12. The implantable medical device of claim 1, further comprising a fixation member configured to secure the implantable medical device within a vasculature of the patient.

13. The assembly of claim 12, wherein fixation member includes two loops formed from a shape memory alloy material.

14. The implantable medical device of claim 1, wherein the implantable medical device is configured for implantation within a pulmonary artery of the patient.

15. A method of assembling an implantable medical device, wherein the implantable medical device includes:
an electrode that forms a first snap-fit attachment area,
an insulator that forms a through-hole, a second snap-fit attachment area and a third snap-fit attachment area, wherein the second snap-fit attachment area is configured to mate with the first snap-fit attachment area of the electrode, and
a body including an elongated conductive housing and a feedthrough wire extending therefrom, wherein the body forms a fourth snap-fit attachment area on one end that is configure to mate with the third snap-fit attachment area of the insulator,
wherein the housing encloses at least one of a battery, a sensor, and an electronic circuit,
wherein the method comprises:
securing the insulator to the body by mating the third snap-fit attachment area of the insulator with the fourth snap-fit attachment area of the body to form an assembly including the insulator and the body with the feedthrough wire extending through the through-hole of the insulator; and
securing the electrode to the assembly including the insulator and the body by mating the first snap-fit attachment area of the electrode with the second snap-fit attachment area of the insulator, wherein the insulator functions to electrically isolate the electrode from the housing of the body.

16. The method of claim 15, wherein the electrode forms a hole, the method further comprising, injecting an adhesive into the hole filling cavities between the electrode, the insulator and the body to further secure the electrode to the body.

17. The method of claim 15, wherein the electrode forms a hole that receives the feedthrough wire of the body when the electrode is secured to the assembly including the insulator and the body by mating the first snap-fit attachment area of the electrode with the second snap-fit attachment area of the insulator.

18. The method of claim 15,
wherein the housing encloses at least one of the sensor and the electronic circuit, the method further comprising securing the battery to the body on an opposite end of the housing relative to the electrode,
wherein the battery includes a battery feedthrough serving as a first battery terminal for the battery,
wherein the method further comprises electrically connecting the battery feedthrough to the components enclosed within the housing; and
wherein the battery includes a conductive battery case serving as a second battery terminal of the battery, wherein the method further comprises electrically and mechanically coupling the battery case to the housing of the body.

19. The method of claim 15, wherein the implantable medical device includes the sensor, wherein the sensor selected from a group consisting of:
a pressure sensor;
a cardiac electrogram sensor;
an ECG sensor
a fluid flow sensor;
perfusion sensor
an oxygen sensor;
a carbon dioxide sensor;
an acidity sensor;

an accelerometer;
a glucose sensor;
a blood plasma sensor;
a potassium sensor; and
a temperature sensor.

\* \* \* \* \*